United States Patent [19]

Wierenga

[11] 4,423,228

[45] Dec. 27, 1983

[54] PROCESS FOR PREPARING N-(METHYL-SULFONYL)-1,2,8,8A-CYCLOPROPA[c]BENZO[1,2-b:4,3-b']DIPYRROL-4(5H)-ONE

[75] Inventor: Wendell Wierenga, Kalamazoo, Mich.

[73] Assignee: The Upjohn Company, Kalamazoo, Mich.

[21] Appl. No.: 346,460

[22] Filed: Feb. 8, 1982

Related U.S. Application Data

[62] Division of Ser. No. 207,838, Nov. 18, 1980, abandoned.

[51] Int. Cl.³ .......................................... C07D 487/04
[52] U.S. Cl. .................................. 548/421; 548/433
[58] Field of Search ............................. 548/421, 433

[56] References Cited

U.S. PATENT DOCUMENTS 4,169,888  10/1979  Hanka et al. .................... 424/121

OTHER PUBLICATIONS

Martin, D. G., et al., *J. Antibiot.* 33, 902 (1980).
W. Theilheimer, Synthetic Methods of Organic Chemistry, vol. 31, No. 499 (1977).
R. Appel, Angew. Chem. Internatl., Edit., vol. 14 (1975), No. 12, 801–811.

*Primary Examiner*—Donald G. Daus
*Assistant Examiner*—M. C. Eakin
*Attorney, Agent, or Firm*—Roman Saliwanchik

[57] ABSTRACT

Novel antibacterially-active compound, 1,2,8,8a-cyclopropa[c]benzo[1,2-b:-4,3-b']dipyrol-4(5H)-one, prepared by a novel chemical process. This compound, as well as antibacterially-active intermediates, can be used to eradicate or control susceptible bacteria, for example, *B. subtilis, K. pneumonia, S. lutea, S. aureus,* and *M. avium*.

Included is a process for the preparation of an intermediate compound of the formula

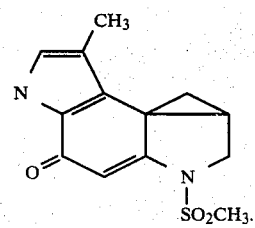

1 Claim, No Drawings

PROCESS FOR PREPARING N-(METHYL-SULFONYL)-1,2,8,8A-CYCLO-PROPA[c]BENZO[1,2-b:4,3-b']DIPYRROL-4(5H)-ONE

This is a division, of application Ser. No. 207,838, filed Nov. 18, 1980, now abandoned.

DESCRIPTION

BACKGROUND OF THE INVENTION

Antibiotic CC-1065, is disclosed and claimed by its chemical and physical parameters in U.S. Pat. No. 4,169,888. Subsequently, the structure of antibiotic CC-1065 was elucidated as disclosed in "Structure Proof of Antibiotic CC-1065", D. G. Martin, C. G. Chidester, D. J. Duchamp, and S. A. Mizsak, *J. Antibiot.*, 33 902 (1980). The structure of antibiotic CC-1065 is shown in CHART 1. Antibiotic CC-1065 consists of a 3-fragment system with the most labile portion of the molecule being the fragment named 1,2,8,8a-cyclopropa[c]benzo[1,2-b:4,3-b']dipyrol-4(5H)-one, which is denoted herein as compound(12). Attempts to obtain this fragment by degradation of antibiotic CC-1065 have failed. Thus, there is no known prior art method to obtain compound(12).

BRIEF SUMMARY OF THE INVENTION

Compound(12) of the subject invention can be made by an 11-step process disclosed in CHART 2. This compound, as well as certain intermediates disclosed herein, are active against certain bacteria, for example, *Bacillus subtilis, Klebsiella pneumonia, Sarcina lutea, Staphylococcus aureus,* and *Mycobacterium avium.* Accordingly, these compounds can be used to disinfect washed and stacked food utensils contaminated with *S. aureus.* Further, the antibacterially-active compounds of this invention can be used as bacteriostatic rinses for laundered clothes, and for impregnating papers and fabrics; and, they are also useful for suppressing the growth of sensitive organisms in plate assays and microbiological media. In general, the antibacterially-active compounds of this invention can be used in the same manner as disclosed for antibiotic CC-1065 in U.S. Pat. No. 4,169,888. These uses are well-known in the antibiotic art. Accordingly, bacteriological techniques are readily available to persons skilled in this art to practice such uses.

DETAILED DESCRIPTION OF THE INVENTION

As disclosed above, the 11-step process for preparing compound (12) is shown in Chart 2. These steps are as follows:

Step 1

The first step (aromatic nucleophilic substitution) in the synthetic approach is described by J. Bourdais and C. Mahieu, *Compt. Redux* [C], 263, 84 (1966). Also see J. Bourdais and C. Germain, *Tet. Letters*, 195 (1970). The various $R_1$ groups can be introduced on the phenol precursor of (1) by procedures described in the literature (appropriate references detailed under step 8). The various malonates, β-keto esters, and β-diketones employed are all known compounds.

Step 2

Reduction. When $R_2$=alkoxy, diisobutylaluminum hydride is the reagent of choice. Reaction conditions are quite specific (see Example 1) for optimum yields. When $R_2$=alkyl or phenyl, standard reduction procedures employing sodium borohydride can be employed.

Step 3

Functional group interchange. The chemistry described specifically herein is in the case of $X=OSO_2CH_3$. The mesylate or tosylate (for example) can be prepared under standard conditions known in the art employing pyridine (with or without solvent, such as methylene chloride) or other acid acceptors such as trialkylamines (with solvent) and the corresponding sulfonyl chloride. The halogen analogs of 4 can be prepared under standard procedures known in the art such as $Ph_3P/CCl_4$ ($CBr_4$) and N-iodosuccinimide/triphenylphosphine.

Step 4

Reduction-cyclization. This step is a novel preparation of indolines (dihydroindoles). This involves the reduction of the nitro to the amino group with concomitant intramolecular cyclization to give (5). The reduction step described in detail herein utilizes $H_2$, $PtO_2$ in alcohol in the presence of a tertiary amine. These are standard hydrogenation conditions in the art. Palladium or nickel catalysts can also be employed and bases other than a tertiary amine, such as pyridine, can be utilized. Alternate reducing conditions can employ Fe or $TiCl_3$ in acid or $SnCl_2$. This may then require a separate step involving treatment with base to induce the cyclization to (5). An example of a reduction with iron is the use of $Fe/CH_3CO_2H/CH_3CH_2OH$ (G. S. Ponticello and J. J. Baldwin, *J. Org. Chem.,* 44, 4003 (1979). These conditions would be required if $R_1=CH_2Ph$ or $—CH_2CH=CH_2$.

The concept of nitro reduction followed by in situ cyclization to indoles is advanced by A. D. Batcho and W. Leimgruber, German Offen. 2057840 (1971), which is a significant improvement over the older Reissert procedure of reductive cyclization to indoles. (See R. J. Sundberg, *The Chemistry of Indoles,* pp. 176–183. Academic Press, N.Y., 1970).

Step 5

Substitution of labile group. This step is required due to the incompatibility of X with the chemistry of step 8. It involves the replacement of X with an acetate or the conjugate base of a $C_1$–$C_5$ alkyl carboxylic acid under standard conditions (alkali carboxylate in acetone, DMF, or alcohol). Since some hydrolysis can occur when $X=OSO_2CH_3$, the reaction mixture is treated with acetic anhydride prior to isolation of (6).

Step 6

Nitration can be performed under a variety of conditions described in the literature including nitric acid in acetic acid, acetic anhydride, sulfuric acid, acetic acid/$H_2O$, alcohol, and nitroalkanes. The regioselectivity of this reaction is supported by the spectroscopic data obtained.

Step 7

Reduction of the nitro to the amino group follows the same chemical description given in step 4 with the omission of base.

Step 8

Indole synthesis. This procedure is based generally on the indole chemistry of Gassman [P. G. Gassman, et. al., *J. Am. Chem. Soc.,* 96, 5494, 5508, 5512 (1974)]. Several modifications are required which are not disclosed or suggested in Gassman's work. The sequence of the chemical events and some of the intermediates are depicted in CHART 3. The α-thiomethyl esters are known.

This process deviates from the published Gassman route by employing the chlorosulfonium complex, A, and reacting it with the aniline, (6); Gassman prepares the chloroamine of an aniline and reacts it with the thioether in making oxindoles. Secondly, two different bases are employed in the process, whereas Gassman uses two equivalents of the aniline followed by a base$_2$. Although triethylamine, diisopropylethylamine, bis(1,8-dimethyl amino)napthalene, and the like both work for base$_1$ and base$_2$, the preferred for base$_1$ is bis(1,8-dimentylamine)napthalene, and triethylamine for base$_2$. Different solvents such as chloroform, acetonitrile, tetrahydrofuran (THF), and methylene chloride can be used, the latter is preferred. The temperature range is from −50° to −80° and the reaction is run under an inert atmosphere. The cyclization to the oxindole B is best promoted by acid catalysis as described by Gassman (2 N HCl, ether and/or ethyl acetate).

The final reduction to (9) (reductive elimination) can be accomplished with lithium aluminum hydride (as described by Gassman) or diborane type reagents, the latter being far superior. The preferred reagent is $(CH_3)_2S\cdot BH_3$ in THF at room temperature for 24 hours.

Step 9

This deprotection step (removal of $R_1$) is described in detail for $R_1=CH_3$ in Example 8. Although there are a number of procedures described in the art involving methyl ether cleavage, only alkyl mercaptide in hexamethylphosphorictriamide (HMPA) under an inert atmosphere (95°–110°) have been found to be effective [S. C. Welch and A.S.C.P. Rao, *Tet. Letters,* 505 (1977) and T. R. Kelly, H. M. Dali, and W-G. Tsang, *Tet. Letters* 3859 (1977), or $Me_2S\cdot BBr_3$ in dichloroethane (P. G. Willard and C. B. Fryhle, *Tet. Letters,* 3731 (1980)].

When $R_1=CH_2Ph$, standard hydrogenolysis conditions suffice to deprotect ($H_2$, Pd/C) [*Org. Reactions,* 7, 263 (1953)]. When $R_1=CH_2SCH_3$, mercuric chloride in acetonitrile/$H_2O$ removes the ether. (R. A. Holton and R. G. Davis, *Tet. Letters,* 533 (1977). When $R_1=CH_2OCH_3$, moderate acid will generate the phenol-10, such as acetic acid [*J. Med. Chem.,* 9, 1 (1966) or *Synthesis,* 244 (1976)]. In fact, this protecting group may be lost in step 6, however, it can be reintroduced prior to step 7 under standard conditions. When $R_1=-CH_2OCH_2CH_2OCH_3$, the phenol can be generated by $ZnBr_2$ or $TiCl_4$ in $CH_2Cl_2$ [*Tet. Letters,* 809 (1976)]. When $R_1=-CH_2CH=CH_2$, several two-step procedures will deprotect the ether (Pd/C in alcohol/*Ang. Chem. Int. Ed.,* 15, 558 (1976); $SeO_2$, $CH_3CO_2H$ in dioxane/*Tet. Letters,* 2885 (1970); t-BuOK, DMSO followed by $H_2SO_4$ in acetone/*J. Chem. Soc.,* 1903 (1965); RhCl(PPh$_3$)$_3$, DABCO in alcohol followed by pH2 [*J. Org. Chem.,* 38, 3224 (1973)]. When $R_1=-CH_2CH_2Si(R_2)_3$ deprotection is effected by Bu$_4$NF [H. Gerlach, et. al., *Helv. Chim. Acta,* 60, 3039 (1977)].

Step 10

See step 3.

Step 11

This step (when X=Br) is promoted by contact with silica gel as well as occurs on standing in protic solvents. This reaction will also proceed in the presence of such bases as tertiary amines, pyridine, t-butoxide, and the like and weak aqueous bases such as bicarbonate and carbonate.

The following examples are illustrative of the products and process of the invention, but are not to be construed as limiting. All percentages are by weight and all solvent mixture proportions are by volume unless otherwise noted.

EXAMPLE 1

Preparation of the 2-aryl-1,3-propandiol (3) from the aryldiethylmalonate (2)

To 400 ml of THF under N$_2$ cooled in an ice-water bath is added 100 g of DIBAL* (0.70 mole) in 400 ml of toluene. To this stirred solution is added 33.0 g. (0.105 mole) of the arylmalonate (2) in 100 ml of THF. The rate of addition is controlled to keep the reaction temperature below 5°. After the addition is complete the ice bath is removed. The reaction is quenched after 3 hours total reaction time by the portion-wise addition of the solution to cold 3 N HCl with stirring (approximately 1.5 l). The mixture is then extracted with 1 l of EtOAc followed by 1000 ml $CH_2Cl_2$. The combined organic phases are dried over $Na_2SO_4$ and concentrated to a red-brown residue (21.2 g). Chromatography of the residue on 500 g silica gel with 60% EtOAc/hexane→100% EtOAc gradient eluent affords 11.7 g (49% yield) of the diol (3) (U-62,598) as a light red oil (solidifies on standing in the freezer).

*diisobutyl aluminum hydride

NMR (CDCl$_3$): 7.5–7.0 (m, 3H), 3.80 (s, 3H), 4.0–3.3 (m, 7H-includes 2 OH)

MS: Calc. for $C_{10}H_{13}NO_5$: 227.0794. Found: 227.0780.

Analysis: Calc: C, 52.86, H, 5.76, N, 6.16. Found: C, 53.40, H, 5.77, N, 5.99.

EXAMPLE 2

Preparation of the 2-aryl-1,3-propandiol bismesylate (4) from the 2-aryl-1,3-propandiol (3)

To 4.7 g (0.2 moles) of the diol (3) in 100 ml of dry pyridine under N$_2$ at 0°–5° is added with stirring 6.8 g (0.06 mole) of methane-sulfonyl chloride. After stirring at 5° for 30 minutes followed by room temperature for 90 minutes, the solution is concentrated in vacuo, then taken up in $CH_2Cl_2$/1 N HCl. The organic phase is separated, dried over $Na_2SO_4$, concentrated to a residue. Trituration with EtOAc affords an off-white solid and the mother liquors can be chromatographed on silica gel (EtOAc eluent) to afford a total yield of 6.65 g (86% yield), m.p. 122–3° (recrystallized from acetone) of compound(4), bimesylate (U-62,597).

NMR (Acet-d$_6$): 7.7–7.2 (m, 3H), 4.62 (d, 4H, J=J Hz), 4.11 (t, 1H, J=7 Hz), 3.92 (s, 3H), 3.06 (s, 6H).

Analysis: Calc for $C_{12}H_{17}NO_9S_2$. Calc: C, 37.59, H, 4.47, N, 3.65. Found: C, 37.35, H, 4.44, N, 3.59.

This compound was assayed by a standard tube dilution assay against L1210 mouse leukemia cells in culture and gave the following results:

$ID_{90}(\mu g/ml) = 6.0$, $ID_{90}(\mu g/ml) = 18$.

EXAMPLE 3

Preparation of the 6-methoxyindoline bismesylate (5) from the 2-aryl-1,3-propandiol bismesylate (4)

To 1.91 g (0.005 mole) of compound(4) in 30 ml of THF, 20 ml of EtOAc, and 150 ml of absolute ethanol is added 1.5 ml of triethylamine and 400 mg of $PtO_2$. This solution is placed under 7–10 psi $H_2$ pressure with shaking for 30 minutes. The reaction solution is then filtrated over celite and concentrated in vacuo. After several $CH_2Cl_2$ azeotropes in vacuo, the residue is ultimately taken up in 100 ml of $CH_2Cl_2$ and cooled under $N_2$ in an ice bath. To the stirred solution is added 1.5 ml of triethylamine followed by the dropwise addition of 900 μl methane sulfonylchloride. After stirring for 30 minutes, the solution is allowed to come to room temperature for 60 minutes. The solution is then washed with 1 N HCl, dried over $Na_2SO_4$, and concentrated. The residue is rapidly chromatographed on 150 g silica gel with 500 ml of 60% EtOAc/hexane followed by 1000 ml of 80% elution; recovered 1.3 g (78% yield) of an off-white solid, m.p. 122–3° (recrystallized from ethanol) of compound(5), the 6-methoxyindoline bismesylate (U-62,586).

NMR (DMF-$d_7$): 7.36 (d, 1H, J=8.5 Hz), 7.00 (d, 1H, J=2 Hz), 6.69 (dd, 1H, J=2, 8.5 Hz), 4.47 (2H, d, J=6 Hz), 4.3–3.6 (m, 3H), 3.80 (s, 3H), 3.20 (s, 3H), 3.07 (s, 3H).

Analysis: Calc for $C_{12}H_{17}NS_2O_6$. Calc: C, 42.97, H, 5.11, N, 4.18. Found: C, 42.87, H, 5.27, N, 4.29.

This compound was assayed by a standard tube dilution assay against L1210 mouse leukemia cells in culture and gave the following results:

$ID_{50}(\mu g/ml) = 4.8$, $ID_{90}(\mu g/ml) = 10$.

EXAMPLE 4

Preparation of the 6-methoxy indoline acetate (6) from the 6-methoxy indoline bismesylate (5)

To 13.0 g (39 mmol) of the 6-methoxy indoline bismesylate (5) in 30 ml of DMF is added 800 ml of abs. ethanol followed by 32 g of sodium acetate. This hereogeneous solution is refluxed under $N_2$ for 24 hours, cooled, and concentrated in vacuo. The residue is treated with 100 ml of acetic anhydride for 2 hours (stirring at room temperature), then concentrated in vacuo. The residue is taken up in $CH_2Cl_2/H_2O$ and the organic phase is separated, dried over $Na_2SO_4$, filtered through charcoal, and concentrated to an oil which solidifies; 11.6 g of compound(6), the 6-methoxy indoline acetate (100%, if necessary, further purification is possible with silica gel chromatography employing 60% EtOAc/hexane eluent).

NMR (CDCl$_3$): 7.17 (d, 1H, J=8.5 Hz), 7.02 (d, 1H, J=2 Hz), 6.60 (dd, 1H, J=2, 8.5 Hz), 4.18 (d, 2H, J=6 Hz), 4.1–3.4 (m, 3H), 3.78 (s, 3H), 2.91 (s, 3H), 2.05 (s, 3H).

Analysis: Calc for $C_{13}H_{17}NO_5S$. Calc: C, 52.16, H, 5.76, N 4.68. Found: C, 52.13, H, 5.79, N, 5.27.

MS: Calc: 299.0827. Found: 299.0823.

EXAMPLE 5

Preparation of the 5-nitro-6-methoxy indoline acetate (7) from the 6-methoxy indoline acetate (6)

To 500 mg (1.67 mmole) of the 6-methoxy indoline acetate (6) in 20 ml of nitromethane is added 90 μl of 90% $HNO_3$. The cooled reaction solution (0°–5°) is stirred for 30 minutes, then warmed to room temperature for 30 minutes. The solution is diluted with $CH_2Cl_2$ and aqueous sodium bicarbonate. The organic phase is separated, dried over $Na_2SO_4$, and concentrated. The residue is chromatographed on 50 g silica gel (60% EtOAc/hexane eluent→100% EtOAc) yield; 440 mg (76% yield) of a yellow solid, m.p. 175–7° (recrystallized from ethanol) of compound(7), the 5-nitro-6-methoxy indoline acetate (U-62,696).

NMR (DMF-$d_7$): 7.91 (s, 1H), 7.20 (s, 1H), 4.27 (d, 2H, J=6 Hz), 4.3–3.7 (m, 3H), 3.98 (s, 3H), 3.17 (s, 3H), 2.07 (s, 3H).

Analysis: Calc for $C_{13}H_{16}N_2O_7S$. Calc: C, 45.34, H, 4.68, N, 8.14. Found: C, 44.81, H, 4.77, N, 8.16.

This compound was assayed by a standard tube dilution assay against L1210 mouse leukemia cells in culture and gave the following results:

$ID_{50}(\mu g/ml) = >50$, $ID_{90}(\mu g/ml) = >50$.

EXAMPLE 6

Preparation of the 5-amino-6-methoxy indoline acetate (8) from the 5-nitro-6-methoxy indoline acetate (7)

To 4.5 g (13 mmole) of the 5-nitro-6-methoxy indoline acetate (7) in 50 ml of THF and 150 ml of absolute ethanol is added 500 mg $PtO_2$ and shaken under 10 psi of $H_2$ until uptake ceases (approximately 60 minutes). Filter and concentrate in vacuo. Upon concentration, 3.0 g of product precipitates out. This is filtered off and the mother liquors rapidly chromatographed on 100 g silica gel with EtOAc eluent to afford an additional 0.6 g. The total yield (3.6 g) is 88%; m.p. 134–5° (from acetone/cyclohexane) of compound(8), the 5-amino-6-methoxy indoline acetate (U-62,697).

NMR (CDCl$_3$): 7.02 (s, 1H), 6.65 (s, 1H), 4.16 (d, 2H, J=6 Hz), 4.1–3.5 (m, 3H), 3.83 (s, 3H), 3.6 (br. s, 2H), 2.83 (s, 3H).

Analysis: Calc for $C_{13}H_{18}N_2O_5S$. Calc: C, 49.67, H, 5.77, N, 8.91. Found: C, 49.74, H, 5.72, H, 8.94.

This compound was assayed by a standard tube dilution assay against L1210 mouse leukemia cells in culture and gave the following results:

$ID_{50}(\mu g/ml) = >50$, $ID_{90}(\mu g/ml) = >50$.

EXAMPLE 7

Preparation of the 4,5-pyrrolo-6-methoxy indoline (9) from the 5-amino-6-methoxy indoline acetate (8)

To 14 ml of dry $CH_2Cl_2$ under $N_2$ at −75° is added 6.0 ml of a $Cl_2/CH_2Cl_2$ solution (20 μl $Cl_2$/ml $CH_2Cl_2$). To this stirred solution is added 370 μl (2.5 mmole) of $CH_3(CH_3S)CHCO_2C_2H_5$ (prepared from $CH_3(Br)CHCO_2C_2H_5$ and methyl mercaptide by the procedure of E. H. Wick, T. Yamanishi, H. C. Wertheimer, Y. E. Hoff, B. F. Proctor, and S. A. Goldblith, *J. Agr. Food Chem.*, 9, 289 (1961)). After 5 minutes a solution of 470 mg (2.2 mmole) of 1,8-bisdimethylaminonapthalene and 628 mg (2.0 mmole) of the anilinoindoline (8) in 3.0 ml of dry $CH_2Cl_2$ is added dropwise over 15 minutes. The red solution is stirred for 2 hours at −75°, then 350 μl of triethylamine in 650 μl of CH₂Cl₂ is added dropwise over several minutes. The cooling bath is removed. When the reaction solution reaches room temperature it is briefly concentrated in vacuo. To the residue is added 5 ml EtOAc, 25 ml of ether and 6 ml of 2 N HCl and stirred vigorously for 2 hours. The organic phase is separated and the aqueous is extracted with 1:1 EtOAc/Et₂O. The organics are combined, dried over Na₂SO₄ and concentrated. At this point the residue is taken up in 10 ml of THF and treated with 3.0 ml of 2 M $BH_3.SMe_2$ overnight at room temperature under $N_2$. Alternatively the diasteromeric oxindoles (B) derived from the acid treatment can be isolated at this point by silica gel chromatography (50 g; 60% EtOAc/hexane to 90% EtOAc/hexane).

GS-MS: m/e M⁺ 414 (15%), 227 (100%)-2' 1% SE-30

NMR(CDCl₃): 8.4 (br. s, 1H), 7.11 (s, 1H), 4.5–3.7 (m, 5H), 3.90 (s, 3H), 2.95 (s, 3H), 2.10 (s, 3H), 1.92 (s, 3H), 1.82 (s, 3H)—major diastereomer (2.5/1); minor diasteromer shows the following differences—1.99 (s, 3H), 1.76 (s, 3H), for —SCH₃ and —CH₃, the NH is is at 7.7 and the CH₂ region is 4.3–3.6 ppm.

The aqueous phase from the acid treatment can be neutralized and extracted with CH₂Cl₂. The CH₂Cl₂ solution can be dried, concentrated, and chromatographed on silica gel with 50% acetone/cyclohexane to give 40% recovery of starting material (anilinoindoline) and 20% deacylated starting material.

The boranedimethylsulfide reductive elimination (on B) reaction is worked up by quenching with 1 N HCl until gas evolution ceases and taking up in CH₂Cl₂/H₂O. The separated organic phase is dried over Na₂SO₄ and concentrated. The residue is chromatographed on silica gel (50% acetone/cyclohexane) to afford 155 mg of product (9); 25% isolated yield—85% based on recovered starting material), m.p. 182°–183° (phase change at 160°, recrystallized from chloroform), the 4,5-pyrrolo-6-methoxy indoline (9) (U-62,233).

NMR (CDCl₃): 8.3 (br. s, 1H), 6.96 (s, 2H), 4.2–3.5 (m, 5H+OH), 3.92 (s, 3H), 2.87 (s, 3H), 2.41 (s, 3H).

Analysis: Calc for $C_{14}H_{18}N_2O_4S$. Calc: C, 54.17, H, 5.84, N, 9.03. Found: C, 53.49, H, 5.96, N, 9.42.

GC-MS: of O-acetate-m/e M⁺ 352 (13%), 213 (100%)-2'-1% SE-30, temperature 150°–260° (10°/minute); single peak This compound was assayed by a standard tube dilution assay against L1210 mouse leukemia cells in culture and gave the following results:

ID₅₀(μg/ml)=>4. ID₉₀(μg/ml)=>4.

EXAMPLE 8

Preparation of the 4,5-pyrrolo-6-hydroxy indoline (10) from the 4,5-pyrrolo-6-methoxy indoline (9)

To 10 ml of dry, degassed HMPA (hexamethylphosphorictriamide) under N₂ at room temperature is added 350 μl of butyl mercaptan. The solution is cooled in an ice-water bath and 2.0 ml of 1.5 M n-BuLi in hexane is added dropwise. After allowing the reaction to come to room temperature 100 mg (0.3 mmole) of the indole (9) is added with stirring. The solution is heated to 100° for 2.5 hours. The reaction is followed by tlc (50% acetone/cyclohexane) and when conversion appears approximately 75% complete (by vanillin/phosphoric acid spray), heating is terminated. The cooled solution is poured into 1 N HCl (100 ml) and extracted with 20 ml EtOAc. The separated organic phase is washed with additional 50 ml of water. The aqueous phases are combined and back-extracted with 20 ml of EtOAc. The organic phases are then combined, dried over Na₂SO₄, concentrated in vacuo, and applied to a 100 g silica gel column and eluted with 50% acetone/cyclohexane. Afforded are 25 mg of starting material and 45 mg of product (10) (44% isolated yield, 69% based on recovered S.M.), the 4,5-pyrrolo-6-hydroxy indoline (U-62,370).

NMR (Acet-d₆): 7.8 (br. s, 1H), 7.03 (s, 1H), 6.83 (s, 1H), 4.25–3.25 (m, 5H), 2.86 (s, 3H), 2.36 (s, 3H)

This product was treated with acetic anhydride (1.0 ml) and 20 mg of NaOAc overnight, then taken up in CH₂Cl₂/H₂O. The organic phase was separated, dried over Na₂SO₄, and concentrated.

NMR (CDCl₃): 7.8 (br. s, 1H), 7.16 (s, 1H), 6.97 (s, 1H), 4.42, 4.20 (dd, 2H), 4.2–3.7 (m, 3H), 2.86 (s, 3H), 2.40 (s, 3H), 2.35 (s, 3H), 2.06 (s, 3H).

GC-MS: m/e M⁺ 380 (25%), 199 (100%)-2'-1% SE-30

This compound was assayed by a standard tube dilution assay against L1210 mouse leukemia cells in culture and gave the following results:

ID₅₀(μg/ml)=>5, ID₉₀(μg/ml)=>5.

EXAMPLE 9

Preparation of the 4,5-pyrrolo-6-hydroxy indoline bromide (11) from the 4,5-pyrrolo-6-hydroxy indoline alcohol (10)

To 25 mg (65 μmole) of the substrate alcohol in 1.0 ml of dry acetonitrile under N₂ at room temperature is added 33 mg (100 μmole) of CBr₄ and 26 mg (100 μmole) of triphenyl phosphine (Ph₃P). After stirring for 30 minutes an additional 11 mg CBr₄ and 8 mg of Ph₃P are added. The reaction is taken up in CH₂Cl₂/H₂O after 60 minutes (total). The organic phase is separated, dried over Na₂SO₄, and concentrated. The residue is placed on three 20×20 cm 250μ silica gel plates and eluted with 50% acetone/cyclohexane. Approximately 8 mg of the higher $R_f$ product (0.64; alcohol $R_f$=0.45) is recovered, compound (11), the 4,5-pyrrolo-6-hydroxy indoline bromide (U-62,694).

NMR (CDCl₃): 8.5 (br. s, 1H), 7.1 (s, 1H), 6.9 (s, 1H), 4.23 (d, 2H, J=6 Hz), 4.0–3.5 (m, 3H), 2.89 (s, 3H), 2.38 (s, 3H).

Beilstein test: positive

MS: Calc. for $C_{16}H_{23}N_2O_3{}^{79}BrSSi$=430.0382, Found 430.0375 (mono-TMS); m/e M⁺ 430/432 (14%), 271 (90%), 147 (100%).

This compound was assayed by a standard tube dilution assay against L1210 mouse leukemia cells in culture and gave the following results:

ID₅₀(μg/ml)=0.12, ID₉₀(μg/ml)=0.37.

EXAMPLE 10

Preparation of the 4,5-pyrrolo-6-hydroxy indoline mesylate (11) from the 4,5-pyrrolo-6-hydroxy indoline alcohol (10)

To 20 mg (65 μmole) of the alcohol substrate (10) in 1.0 ml pyridine in an ice bath with stirring under N₂ is added 8 μl of methanesulfonyl chloride (70 μmole). After 30 minutes in additional 2 μl of CH₃SO₂Cl is added and worked up with 2 N HCl/CH₂Cl₂ after 60 minutes total reaction time. The organic phase is separated, dried over Na₂SO₄, and concentrated. Tlc indicates mostly lower $R_f$ product (0.28 in 50% acetone/cyclohexane, alcohol $R_f$=0.46) and some higher $R_f$ product (0.66). Preparative tlc (3-20×20 cm 250μ silica gel plates) affords 2 mg of higher $R_f$ material (NMR indicated only one $CH_3SO_2$ group; it is probably the chloride) and 9 mg of the lower $R_f$ material, compound(11) (U-62,695).

NMR (Acet-$d_6$): 8.6 (br. s, 1H), 6.97 (s, 1H), 6.74 (s, 1H), 4.3 (m, 2H), 4.1-3.6 (m, 3H), 2.96 (s, 3H), 2.79 (s, 3H), 2.26 (s, 3H).

This compound was assayed by a standard tube dilution assay against L1210 mouse leukemia cells in culture and gave the following results:

$ID_{50}(\mu g/ml) = 1.0$, $ID_{90}(\mu g/ml) = 3.3$.

EXAMPLE 11

Preparation of 1,2,8,8a-cyclopropa[c]benzo[1,2-b:4,3-b']dipyrrol-4(5H)-one (12), N-(methylsulfonyl)

In the following procedure to prepare the 4,5-pyrrolo-6-hydroxy indoline bromide (step 10), if the reaction mixture prior to work-up is concentrated in vacuo and applied to thick-layer silica gel plates directly, instead of isolating the higher $R_f$ (0.64) product bromide, a new lower $R_f$ band (0.32) is noted and recovered as compound(12).

NMR (CDCl$_3$): 9.5 (br. s, 1H), 6.83 (dd, $H_a$), 6.34 (s, $H_b$), 4.10 (d, $H_c$), 3.93 (dd, $H_d$), 3.04 (s, 3H), 2.93 (m, $H_e$), 2.00 (d, 3H), 1.97 (dd, $H_f$), 1.37 (dd, $H_g$).

| | |
|---|---|
| $J_{c,e} = 0.0$ Hz | $J_{e,g} = 4.4$ |
| $J_{c,d} = 9.7$ | $J_{f,g} = 4.4$ |
| $J_{d,e} = 4.7$ | $J_{NH,a} = 2.0$ |
| $J_{e,f} = 7.7$ | $J_{a,CH_3} = <1.0$ |

MS: silylation with BSTFA (DMF containing 1% TMS-Cl) gave m/e M$^+$ 386/388 (22, 12% corresponding to product + Me$_3$SiCl)

UV: (methanol) λ224,272,338.

This compound was assayed by a standard tube dilution assay against L1210 mouse leukemia cells in culture and gave the following results:

$ID_{50}(\mu g/ml) = 0.13$, $ID_{90}(\mu g/ml) = 0.42$.

EXAMPLE 12

Alternate preparation of compound(12)

To the 4,5-pyrrolo-6-hydroxy indoline bromide (or mesylate) (0.1 mmole) in 1 ml of methylene chloride is added 0.1 mmole of diisopropylethyl amine and stirred under N$_2$ for 24 hours at room temperature. The reaction solution is taken up in 10 ml of methylene chloride, washed with 0.1 N HCl, dried over Na$_2$SO$_4$, and concentrated to give the desired product. Further purification can be accomplished by silica gel chromatography.

Compound (11) and (12) exhibit antibacterial activity against *B. subtilis, K. pneumonia, S, lutea, S. aureus* and *M. avium*.

Chart 1

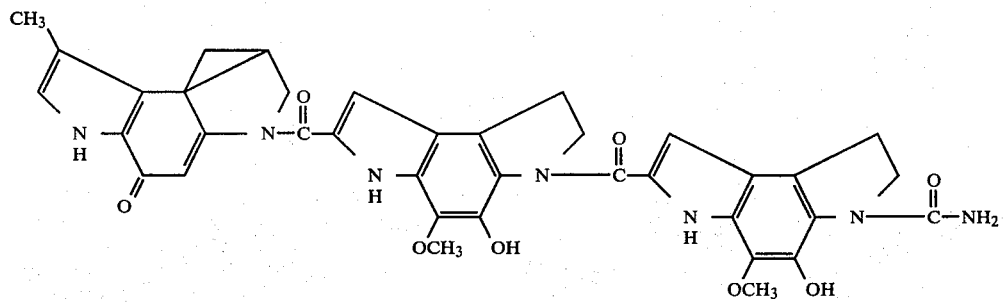

Chart 2

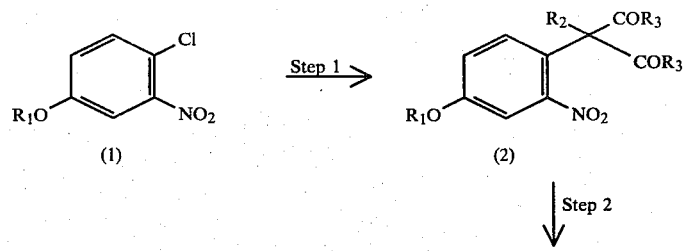

-continued
Chart 2
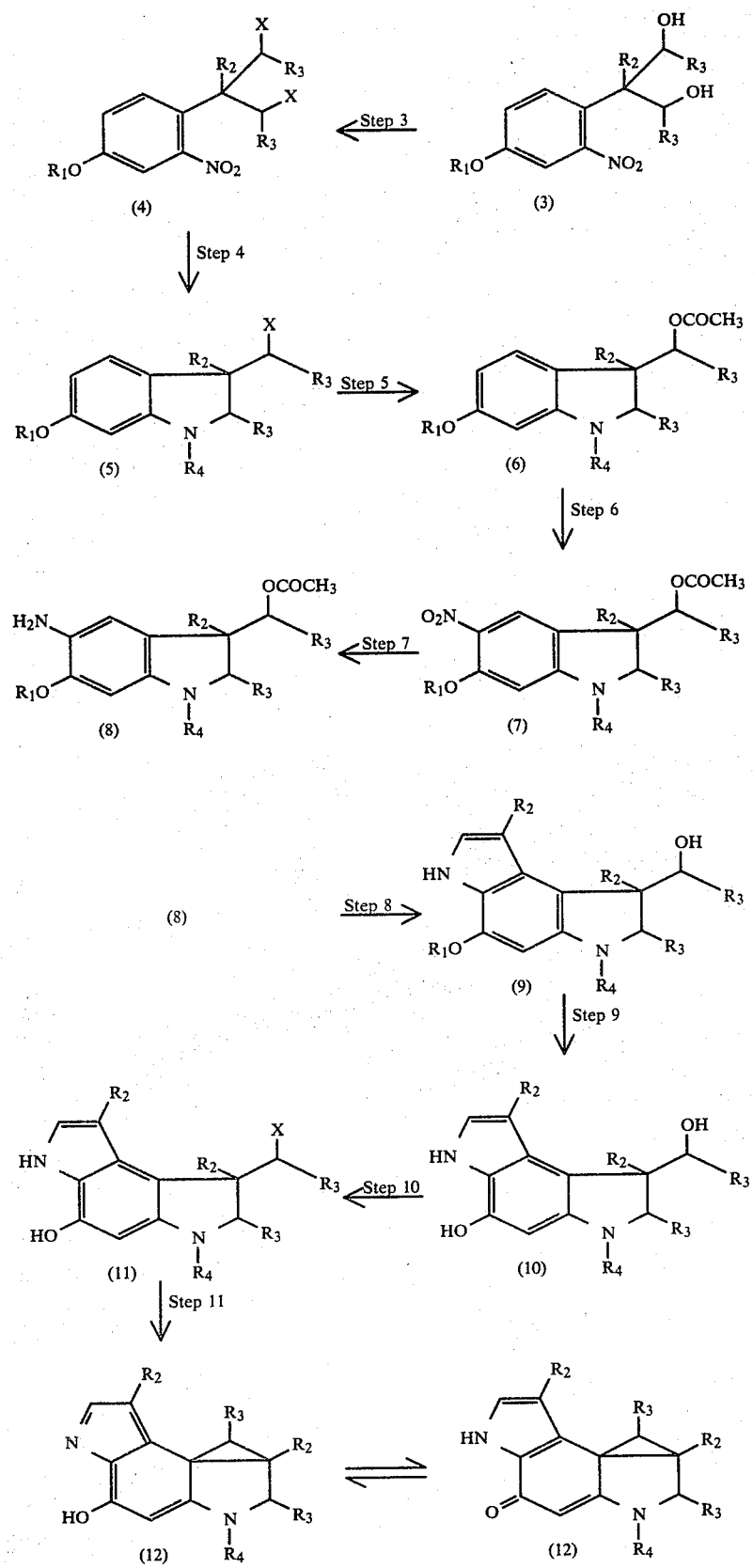

-continued
Chart 2

Definitions:
$R_1$ = $CH_3$—, —$CH_2Ph$, $CH_2$=$CHCH_2$—, —$CH_2SCH_3$, —$CH_2OCH_3$, —$CH_2OCH_2CH_2OCH_3$, —$CH_2CCl_3$, —$CH_2CH_2Si(R_2)_3$
$R_2$ = alkyl ($C_1$-$C_5$), phenyl
$R_3$ = O—alkyl ($C_1$-$C_2$), alkyl ($C_1$-$C_5$), phenyl [Note: $R_3$ = O—alkyl only for compound (2)]
$R_4$ = $SO_2R_2$, $SO_2CH_2COPh$, $CO_2CH_2Z$
X = $OSO_2R_2$, Cl, Br, I
Y = Li, Na, K, MgX
Z = $CH_2I$, $CCl_3$, $CH_2SO_2R_2$, Ph, fluorenylmethyl
As used herein, alkyl of 1 to 2 or 1 to 5 carbon atoms, inclusive, includes methyl, ethyl, propyl, butyl and pentyl, and branched chain isomers thereof.

Chart 3

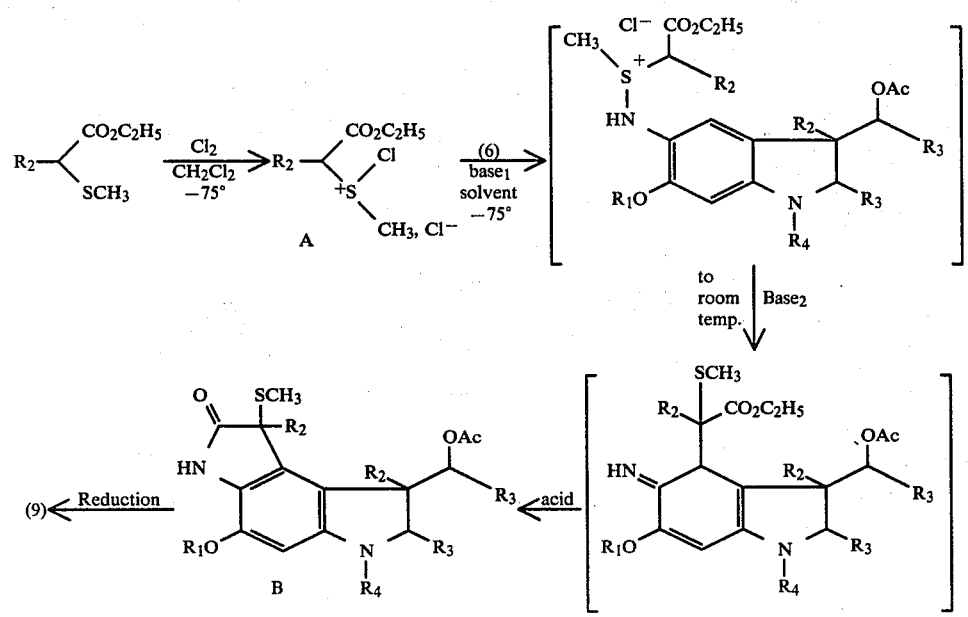

Chart 4

Example 1

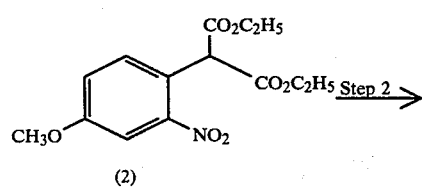

(3)
U-62,598

Example 2

-continued
Chart 4

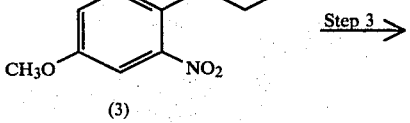

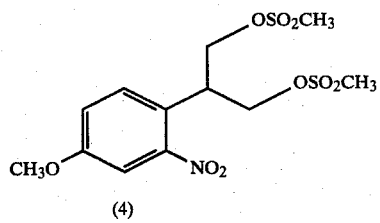

(4)
U-62,597

Example 3

4,423,228
-continued
Chart 4
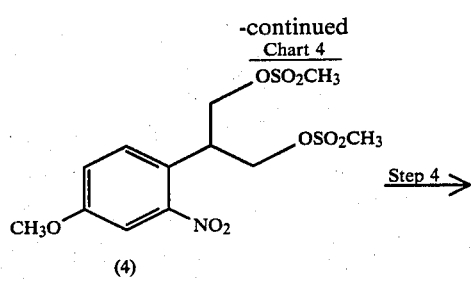
(4)
Step 4 →
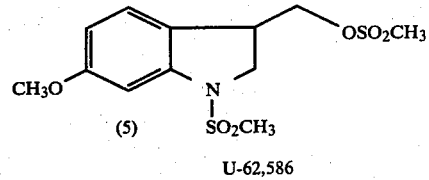
(5) U-62,586
Example 4
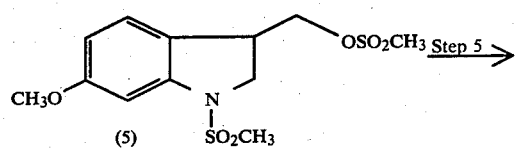
(5)
Step 5 →
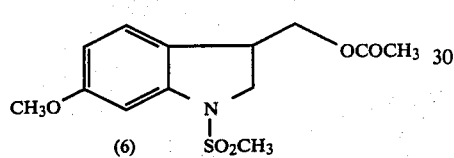
(6)
Example 5
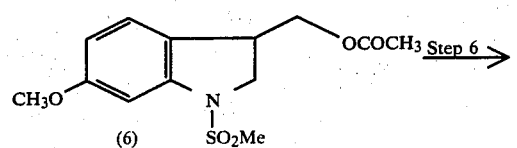
(6)
Step 6 →
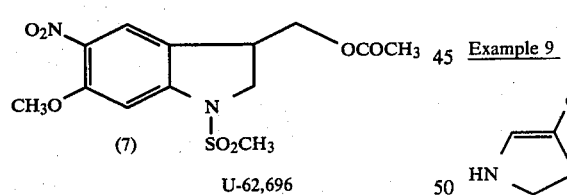
(7) U-62,696
Example 6
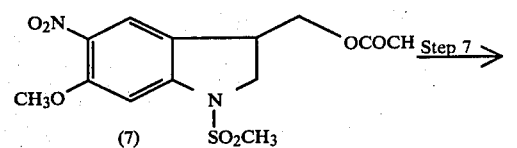
(7)
Step 7 →
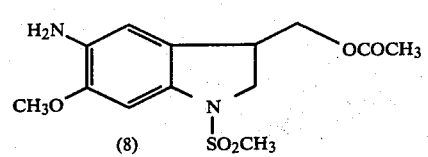
(8) U-62,697
Example 7
-continued
Chart 4
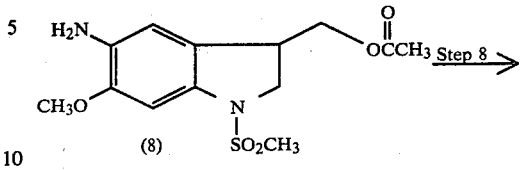
(8)
Step 8 →
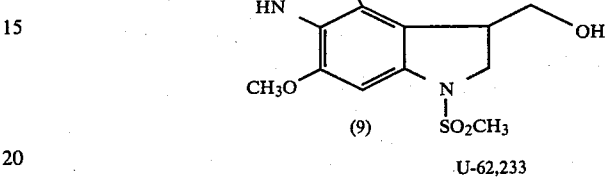
(9) U-62,233
Example 8
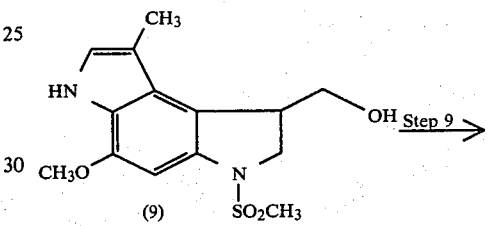
(9)
Step 9 →
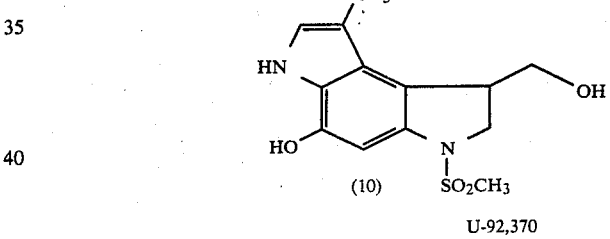
(10) U-92,370
Example 9
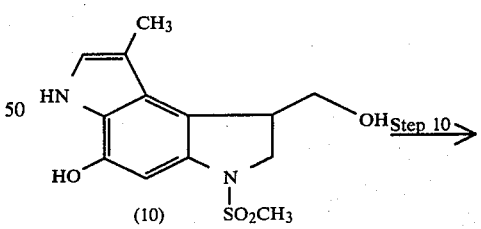
(10)
Step 10 →
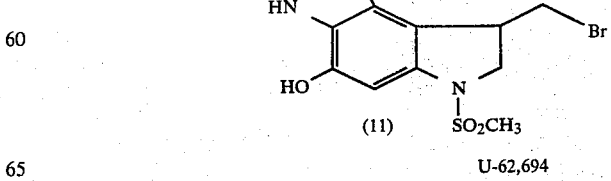
(11) U-62,694
Example 10

-continued
Chart 4

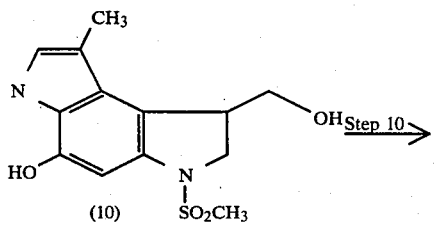

(10)

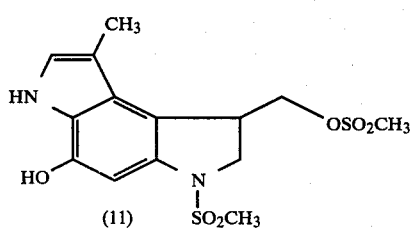

(11)    U-62,695

Example 11

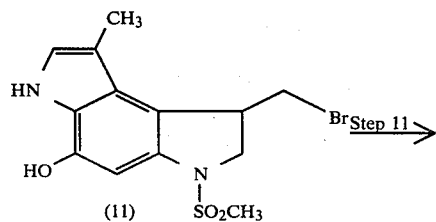

(11)

-continued
Chart 4

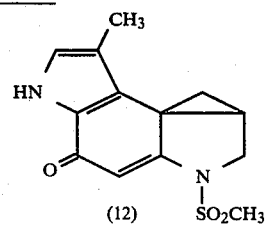

(12)    U-62,736

I claim:
1. A process for preparing a compound of the formula

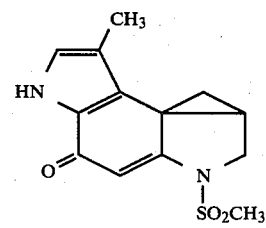

which comprises reacting a compound of the formula with triphenylphosphine/carbon tetrahalide, concentrating the reaction mixture in vacuo to a concentrate, applying said concentrate to a thick-layer silica gel plate, and eluting the desired compound therefrom with a non-polar organic solvent in which the desired compound is soluble.

* * * * *